US00PP32722P2

(12) United States Plant Patent

Vitten et al.

(10) Patent No.: US PP32,722 P2
(45) Date of Patent: Jan. 5, 2021

(54) RASPBERRY PLANT VARIETY NAMED 'DRISRASPSEVENTEEN'

(50) Latin Name: ***Rubus idaeus* L.**
Varietal Denomination: DrisRaspSeventeen

(71) Applicant: Driscoll's, Inc., Watsonville, CA (US)

(72) Inventors: Matthias Vitten, Watsonville, CA (US); Luis Miguel Rodriguez, Watsonville, CA (US); Kyle Rak, Watsonville, CA (US); James Heilig, Watsonville, CA (US)

(73) Assignee: Driscoll's, Inc., Watsonville, CA (US)

( * ) Notice: Subject to any disclaimer, the term of this patent is extended or adjusted under 35 U.S.C. 154(b) by 0 days.

(21) Appl. No.: 16/602,687

(22) Filed: Nov. 19, 2019

(51) Int. Cl.
*A01H 5/08* (2018.01)
*A01H 6/74* (2018.01)

(52) U.S. Cl.
USPC ..... Plt./204
CPC ..... *A01H 6/7499* (2018.05)

(58) Field of Classification Search
USPC ..... Plt./204
CPC ..... A01H 6/7499; A01H 5/08
See application file for complete search history.

(56) References Cited

U.S. PATENT DOCUMENTS

PP4,486 P 11/1979 Reiter
PP6,493 P 12/1988 Wilhelm
PP7,436 P 2/1991 Ackerman
PP7,437 P 2/1991 Ackerman
PP7,528 P 5/1991 Ackerman
PP8,022 P 11/1992 Wilhelm
PP8,027 P 11/1992 Wilhelm
PP9,340 P 10/1995 Wilhelm et al.
PP9,653 P 10/1996 Wilhelm et al.
PP9,696 P 11/1996 Fear
PP11,067 P 9/1999 Fear et al.
PP11,087 P 10/1999 Fear et al.
PP11,094 P 10/1999 Fear et al.
PP11,102 P 10/1999 Fear et al.
PP14,761 P2 5/2004 Fear et al.
PP14,781 P2 5/2004 Fear et al.
PP14,804 P2 5/2004 Fear et al.
PP14,860 P2 6/2004 Fear et al.
PP14,903 P2 6/2004 Fear et al.
PP14,904 P2 6/2004 Fear et al.
PP18,658 P3 3/2008 Fear et al.
PP18,659 P3 3/2008 Fear et al.
PP19,137 P3 8/2008 Harrison et al.
PP19,656 P2 1/2009 Hamilton et al.
PP22,246 P3 11/2011 Hamilton et al.
PP22,731 P2 5/2012 Fear et al.
PP23,477 P3 3/2013 Hamilton et al.
PP24,610 P3 7/2014 Hamilton et al.
PP25,044 P3 11/2014 Hamilton et al.
PP25,045 P3 11/2014 Hamilton et al.
PP27,644 P3 2/2017 Hamilton et al.
PP28,775 P2 12/2017 Hamilton et al.
PP28,856 P3 1/2018 Vitten et al.
PP29,402 P2 6/2018 Vitten et al.
PP30,577 P2 6/2019 Vitten et al.
PP30,733 P2 7/2019 Hamilton et al.

OTHER PUBLICATIONS

Cousineau et al., "Use of Isoenzyme Analysis to Characterize Raspberry Cultivars and Detect Cultivar Mislabeling", HortScience vol. 27, No. 9, Sep. 1992, pp. 1023-1025.
Hamilton et al., Unpublished U.S. Appl. No. 16/350,839, filed Jan. 22, 2019, titled "Raspberry Plant Variety Named 'DrisRaspFourteen'".
Vitten et al., Unpublished U.S. Appl. No. 16/501,853, filed Jun. 19, 2019, titled "Raspberry Plant Variety Named 'DrisRaspFifteen'".
Williams et al., "DNA Polymorphisms Amplified by Arbitrary Primers are useful as Genetic Markers", Nucleic Acids Research, vol. 18, No. 22, 1990, pp. 6531-6535.

*Primary Examiner* — Keith O. Robinson
(74) *Attorney, Agent, or Firm* — Morrison & Foerster LLP

(57) ABSTRACT

A new and distinct variety of raspberry plant named 'DrisRaspSeventeen', particularly selected for its primocane and floricane yield, fruit flavor, and sugar content, is disclosed.

4 Drawing Sheets

LATIN NAME

Botanical classification: *Rubus idaeus* L.

VARIETAL DENOMINATION

The varietal denomination of the claimed variety of raspberry plant is 'DrisRaspSeventeen'.

BACKGROUND OF THE INVENTION

Raspberries are the edible fruit of a multitude of plant species in the genus *Rubus* of the rose family. Most raspberry species are in the subgenus *Idaeobatus*. Raspberry plants are perennial plants with woody sterns. Many of the most important modern commercial red raspberry cultivars derive from hybrids between *R. idaeus* and *R. strigosus*. Recent breeding has resulted in cultivars that are thornless and more strongly upright, not needing staking.

Both the red and the black raspberry species have albino-like pale-yellow natural or horticultural variants. Fruits from such plants are called golden raspberries or yellow raspberries. Most pale-fruited raspberries commercially sold in the eastern United States are derivatives of red raspberries. Yellow-fruited variants of the black raspberry are sometimes grown in home gardens. Despite their dissimilar appearance, golden raspberries retain the distinctive flavor of their respective red or black species.

An individual raspberry fruit is made up of around 100 drupelets, each of which contains a juicy pulp and a single central seed. A raspberry bush can yield several hundred berries a year. Unlike blackberries and dewberries, a raspberry has a hollow core once it is removed from the receptacle.

Raspberries are traditionally planted in the winter as dormant canes, but planting plugs produced by tissue culture is also common. Additionally, the long cane production method consists of growing canes for one year in cold climates where the bud break is early, and then transplanting the canes to warm climates where they quickly flower and can produce an early season crop. A very vigorous crop, raspberries spread well and can be considered invasive, using extended underground shoots (also known as suckers or basal shoots) that can develop roots and individual plants.

Raspberries are a popular fruit that are recognized for their antioxidants, high fiber, and as a good source of vitamin C. Raspberry fruit is typically consumed as fresh fruit, individually quick frozen (IQF) fruit, or in prepared foods, such as purées, juices, jellies, jams, grocery items, baked goods, and snack foods.

Raspberry is an important and valuable commercial fruit crop, widely grown in all temperate regions of the world. Accordingly, there is a need for new varieties of raspberry plant. In particular, there is a need for improved varieties of raspberry plant that are stable, high yielding, and agronomically sound.

SUMMARY OF THE INVENTION

In order to meet these needs, the present invention is directed to an improved variety of raspberry plant. In particular, the invention relates to a new and distinct variety of raspberry plant (*Rubus idacus* L.), which has been denominated as 'DrisRaspSeventeen'.

Raspberry plant variety 'DrisRaspSeventeen' was discovered in Santa Cruz County, Calif. in May of 2013 and originated from a cross between the proprietary female parent 'RB626.1' (unpatented) and the proprietary male parent 'RF399.3' (unpatented). The original seedling of the new variety was first asexually propagated in Santa Cruz County, Calif. via root cuttings in July of 2013.

'DrisRaspSeventeen' was subsequently asexually propagated via root cuttings, and underwent further testing in Santa Cruz County, Calif. for six years (2013 to 2019). The present variety has been found to be stable and reproduce true to type through successive asexual propagations via root cuttings.

'DrisRaspSeventeen' exhibits the following distinguishing characteristics over similar raspberry varieties when grown under normal horticultural practices in Santa. Cruz County, Calif.:

1. Predominantly three leaflets per leaf;
2. Conical fruit shape; and
3. Soft fruit.

'DrisRaspSeventeen' was particularly selected for its primocane and floricane yield, fruit flavor, and sugar content.

BRIEF DESCRIPTION OF THE DRAWINGS

This new raspberry plant is illustrated by the accompanying photographs. The colors shown are as true as can be reasonably obtained by conventional photographic procedures. The photographs are of plants that are from one to two years old.

DETAILED BOTANICAL DESCRIPTION

Figure 1:
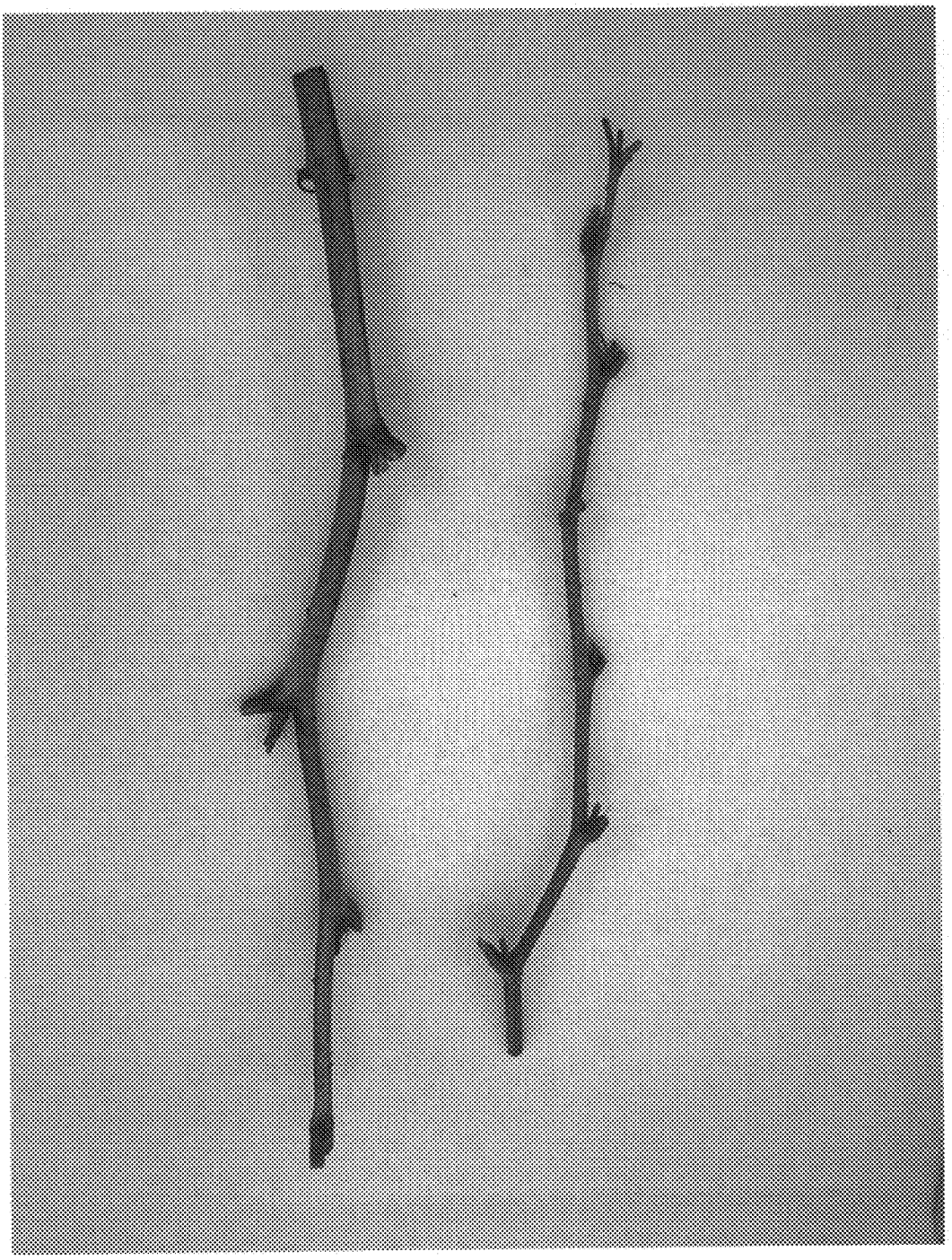
FIG. 1 illustrates sections of canes of raspberry variety 'DrisRaspSeventeen'.
Figure 2:
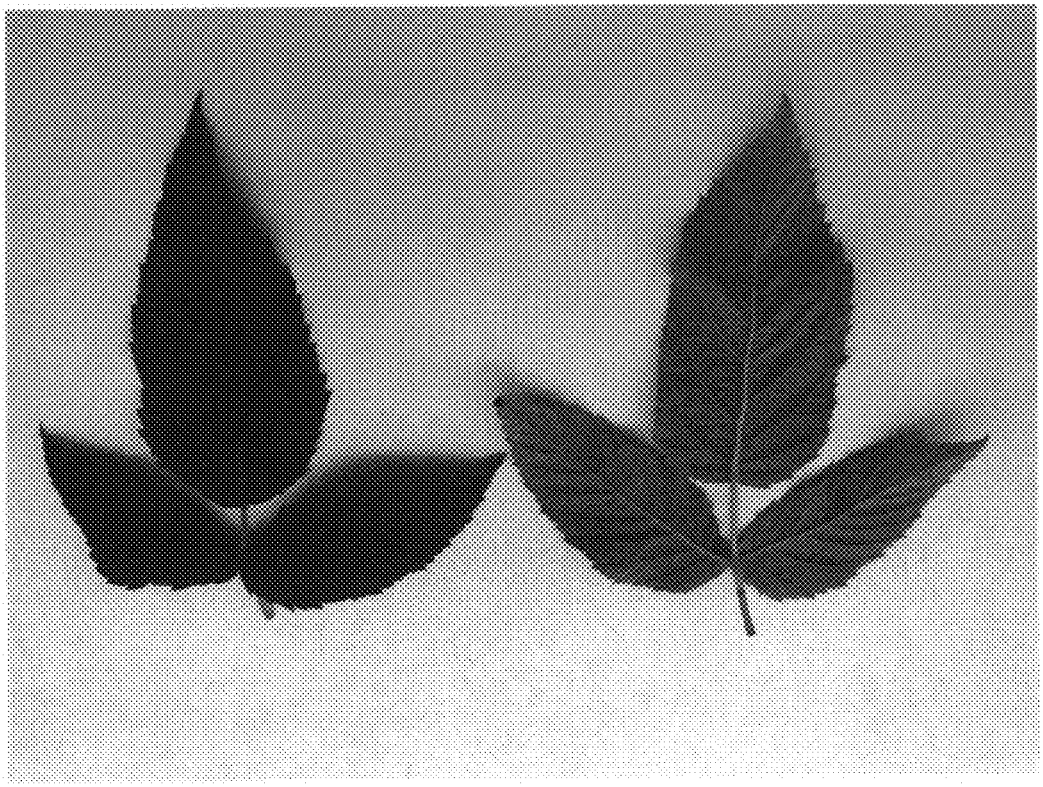
FIG. 2 illustrates the upper surface (left leaf) and the lower surface (right leaf) of leaves of raspberry variety 'DrisRaspSeventeen'.
Figure 3:
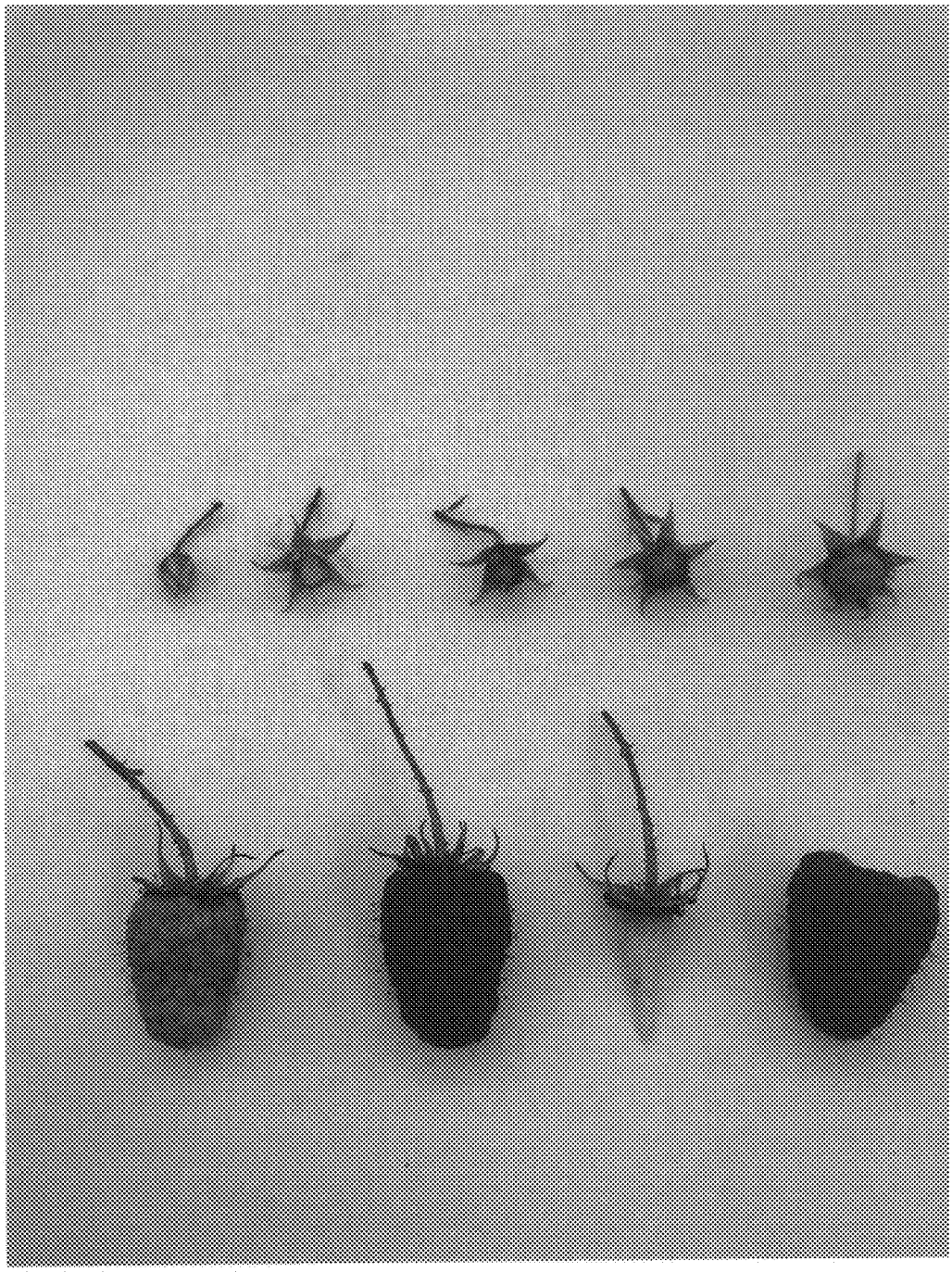
FIG. 3 illustrates flowers and fruit of raspberry variety 'DrisRaspSeventeen' at various stages of development.
Figure 4:
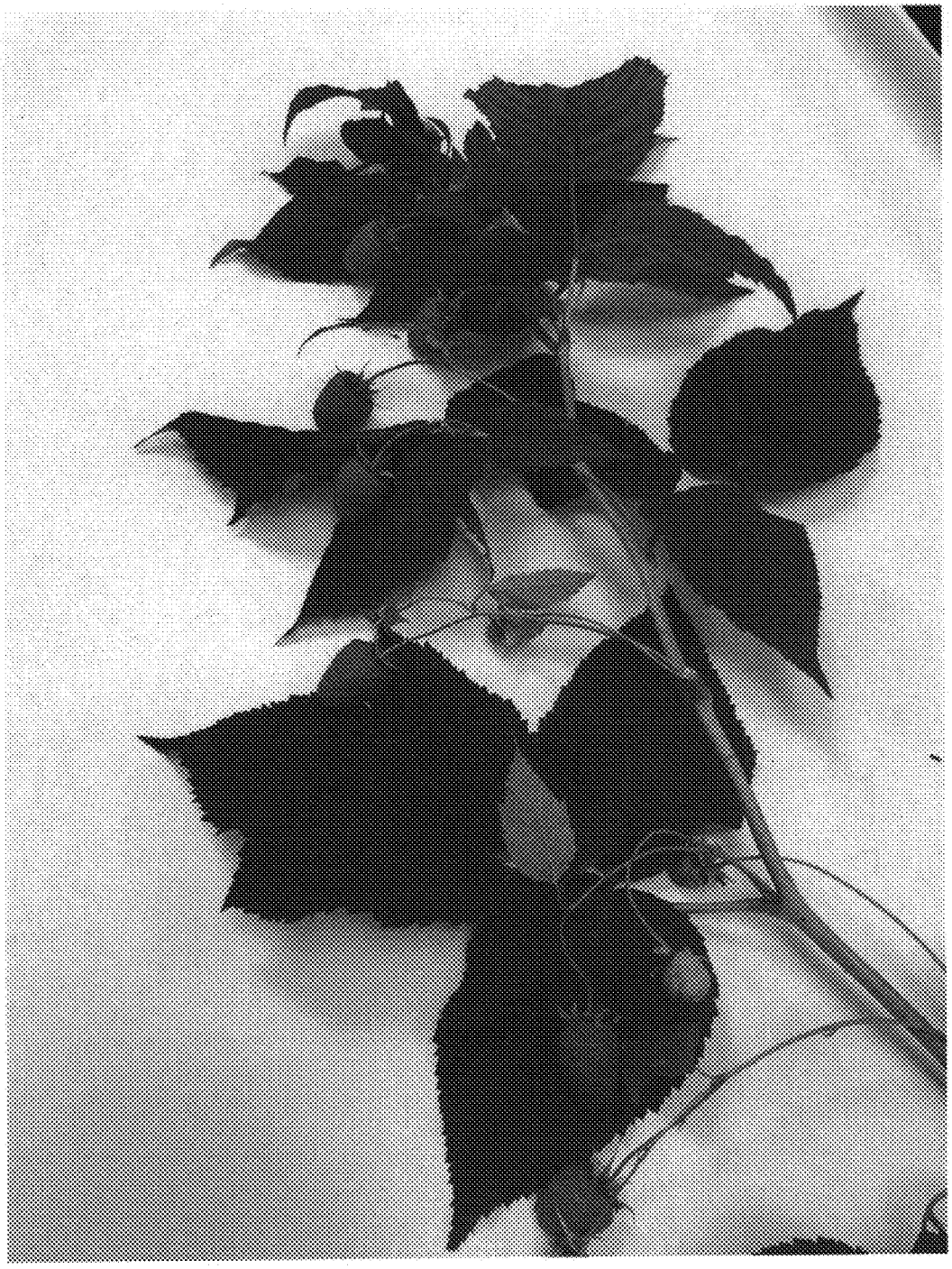
FIG. 4 illustrates a section of a plant of raspberry variety 'DrisRaspSeventeen'.

The following descriptions set forth the distinctive characteristics of 'DrisRaspSeventeen'. Unless where otherwise noted, the data that define these characteristics are based on observations taken from 'DrisRaspSeventeen' plants that were one to two years old, grown in Santa Cruz County, Calif. from 2013 to 2019. These descriptions are in accordance with UPOV terminology. Color designations, color descriptions, and other phenotypical descriptions may deviate from the stated values and descriptions depending upon variation in environmental, seasonal, climatic and cultural conditions. 'DrisRaspSeventeen' has not been observed under all possible environmental conditions. The indicated values represent averages calculated from measurements of several plants. Color references are primarily to The R.H.S. Colour Chart of The Royal Horticultural Society of London (R.H.S.) (2015 edition). Descriptive terminology follows *the Plant Identification Terminology, An Illustrated Glossary*, 2$^{nd}$ edition by James G. Harris and Melinda Woolf Harris, unless where otherwise defined.

Classification:

*Family.*—Rosaceae.

*Botanical.*—*Rubus idacus* L.

*Common name.*—Raspberry.

*Variety name.*—'DrisRaspSeventeen'.

Parentage:

*Female parent.*—'RB626.1' (unpatented).

*Male parent.*—'RF399.3' (unpatented).

Plant:

*Height.*—188.6 cm.

*Width.*—132.9 cm.

*Length/width ratio.*—1.4.

*Growth habit.*—Semi-upright.

*Primocane* (*current year's cane*).—Cane length in autumn:194 cm. Internodal distance at central ⅓ of cane: 5.88 cm. Anthocyanin coloration of cane: Weak. Average number of canes: 15 per meter.

*Very young shoot.*—Anthocyanin coloration of apex during rapid growth: Absent.

*Floricane* (*previous year's cane*).—Dormant cane color: RHS 199B (Greyish brown). Dormant cane length: 160 cm. Fruiting lateral attitude: Semi-erect. Fruiting lateral length: 91.60 cm.

*Prickles* (*spines*).—Length at 1 m height at end of harvest (from base to tip): 1.17 mm. Color: RHS N77 (Purple). Density: Sparse.

Leaves:

*Predominant number of leaflets.*—Three.

*Profile of leaflets in cross section.*—Straight.

*Color of upper surface.*—RHS 135A (Dark green).

*Color of lower surface.*—RHS 135C (Strong yellowish green).

*Rugosity.*—Medium.

*Terminal leaflet.*—Length: 121.5 mm. Width: 92.6 mm. Length/width ratio: 1.3.

*Lateral leaflets.*—Length (basal pair): 82.7 mm. Width (basal pair): 52.5 mm. Length/width ratio (basal pair): 1.6. Relative position of lateral leaflets: Free.

*Rachis length between terminal leaflet and adjacent lateral leaflets.*—37.4 mm.

*Petiole.*—Length: 62.3 mm. Width (measured at mid-length of petiole): 2.34 mm.

Flowers:

*Diameter.*—30.91 mm.

*Petal.*—Length: 8.31 mm. Width: 2.65 mm. Length/width ratio: 3.1.

*Pedicel.*—Length: 62.48 mm. Diameter: 0.93 mm.

*Peduncle.*—Anthocyanin coloration: Absent.

Fruit:.

*Length.*—23.53 mm

*Diameter.*—21.67 mm.

*Length/width ratio.*—1.1.

*General shape in lateral view.*—Conical.

*Color.*—RHS 46A (Strong red).

*Firmness.*—Soft.

Production:

*Main bearing type.*—Both on floricane (previous year's cane) in summer and on primocane (current year's cane) in autumn.

*Primocane* (*current year's cane*).—Time of cane emergence: Early February. Time of beginning of flowering: Early to mid-June. Time of beginning of fruit ripening: Early to mid-July. Length of fruiting period: Early July to late October. Yield: 20,366 kg to 31,654 kg of fruit per hectare per season from 7-month-old plants when grown in Watsonville, Calif.

*Floricane* (*previous year's cane*).—Time of vegetative bud burst: Late March. Time of beginning of flowering: Early April. Time of beginning of fruit ripening: Early May. Length of fruiting period: Early May to late July. Yield: 22,431 kg to 30,227 kg of fruit per hectare per season from 12-month-old plants when grown in Watsonville, Calif.

COMPARISONS TO PARENTAL AND COMMERCIAL RASPBERRY VARIETIES

'DrisRaspSeventeen' differs from the female parent 'RB626.1' (unpatented) in that fruit of 'DrisRaspSeventeen' has improved flavor, higher sugar levels, and better shelf-life when compared with fruit of 'RB626.1'.

'DrisRaspSeventeen' differs from the male parent 'RF399.3' (unpatented) in that fruit of 'DrisRaspSeventeen' has improved flavor, larger fruit size, and higher yield when compared with fruit of 'RF399.3'.

'DrisRaspSeventeen' differs from the commercial raspberry variety 'Driscoll Maravilla' (U.S. Plant Pat. No. 14,804) in that 'DrisRaspSeventeen' has predominantly three leaflets per leaf, whereas 'Driscoll Maravilla' has predominantly five leaflets per leaf. Moreover, 'DrisRaspSeventeen' has a free relative position of lateral leaflets, whereas 'Driscoll Maravilla' has an overlapping relative position of lateral leaflets. In addition, 'DrisRaspSeventeen' has a conical fruit shape, whereas 'Driscoll Maravilla' has a broad conical (ovate) fruit shape. Further, 'DrisRaspSeventeen' has soft fruit, whereas 'Driscoll Maravilla' has firm fruit.

'DrisRaspSeventeen' differs from the commercial raspberry variety 'DrisRaspSeven' (U.S. Plant Pat. No. 25,045) in that 'DrisRaspSeventeen' has purple spines, whereas 'DrisRaspSeven' has dark greyed-orange spines. Moreover, 'DrisRaspSeventeen' has predominantly three leaflets per leaf, whereas 'DrisRaspSeven' has predominantly five leaflets per leaf. In addition, 'DrisRaspSeventeen' has a conical fruit shape, whereas 'DrisRaspSeven' has a long conical fruit shape. Further, 'DrisRaspSeventeen' has soft fruit, whereas 'DrisRaspSeven' has medium firm fruit.

What is claimed is:

1. A new and distinct variety of raspberry plant designated 'DrisRaspSeventeen' as shown and described herein.

* * * * *